(12) United States Patent
Cohen

(10) Patent No.: US 10,709,746 B2
(45) Date of Patent: Jul. 14, 2020

(54) COMPOSITIONS AND METHODS FOR TREATING MEMORY LOSS AND DIMINISHED COGNITION

(71) Applicant: Script Essentials, LLC, Broomfield, CO (US)

(72) Inventor: Suzy Cohen, Broomfield, CO (US)

(*) Notice: Subject to any disclaimer, the term of this patent is extended or adjusted under 35 U.S.C. 154(b) by 308 days.

(21) Appl. No.: 15/992,711

(22) Filed: May 30, 2018

(65) Prior Publication Data
US 2018/0369306 A1 Dec. 27, 2018

Related U.S. Application Data

(60) Provisional application No. 62/512,513, filed on May 30, 2017.

(51) Int. Cl.

| | | |
|---|---|---|
| A61K 36/00 | (2006.01) |
| A61K 36/07 | (2006.01) |
| A61K 36/68 | (2006.01) |
| A61K 36/16 | (2006.01) |
| A61K 36/23 | (2006.01) |
| A61K 31/685 | (2006.01) |
| A61P 25/28 | (2006.01) |
| A61K 31/353 | (2006.01) |
| A61K 31/221 | (2006.01) |
| A61K 31/714 | (2006.01) |
| A61K 9/20 | (2006.01) |
| A61K 9/48 | (2006.01) |
| A61K 31/4748 | (2006.01) |
| A23L 33/175 | (2016.01) |
| A23L 33/15 | (2016.01) |
| A23L 33/105 | (2016.01) |
| A23L 33/00 | (2016.01) |
| A23L 33/10 | (2016.01) |

(52) U.S. Cl.
CPC ........... *A61K 36/07* (2013.01); *A23L 33/00* (2016.08); *A23L 33/10* (2016.08); *A23L 33/105* (2016.08); *A23L 33/15* (2016.08); *A23L 33/175* (2016.08); *A61K 9/20* (2013.01); *A61K 9/48* (2013.01); *A61K 31/221* (2013.01); *A61K 31/353* (2013.01); *A61K 31/4748* (2013.01); *A61K 31/685* (2013.01); *A61K 31/714* (2013.01); *A61K 36/16* (2013.01); *A61K 36/23* (2013.01); *A61K 36/68* (2013.01); *A61P 25/28* (2018.01); *A61K 9/4858* (2013.01)

(58) Field of Classification Search
CPC .................................................. A61K 36/00
See application file for complete search history.

(56) References Cited

U.S. PATENT DOCUMENTS

| | | | |
|---|---|---|---|
| 2013/0034530 A1* | 2/2013 | Fantz ............... | A23L 33/15 424/94.2 |
| 2015/0209306 A1* | 7/2015 | Bredesen ............ | A61K 31/197 424/94.1 |

\* cited by examiner

*Primary Examiner* — Rosanne Kosson

(57) ABSTRACT

The present disclosure is a compound, a method of making the compound and method of using such compound preferably in the form of a dietary supplement that, when administered, is capable of supporting memory, focus, and clarity. The unique combination of the composition is preferably administered orally. The composition is preferably comprised of at least Hericium Erinaceus, Bacopa Monnieri, ECGC (Epigallocatechin-3-Gallate), Huperzine, Acetyl-L-Carnitine, Vitamin B12, Ginkgo Biloba, Phosphatidylserine, and Gotu Kola, in pre-determined amounts. The composition can further comprise a palliative agent, and can be provided in the form of a capsule, powder, liquid or tablet.

17 Claims, No Drawings

COMPOSITIONS AND METHODS FOR TREATING MEMORY LOSS AND DIMINISHED COGNITION

CROSS-REFERENCE TO RELATED APPLICATION

This application claims priority to and the benefit under 35 U.S.C. § 119(e) to U.S. Provisional Patent Application Ser. No. 62/512,513 filed May 30, 2017, which is incorporated by reference in its entirety.

FIELD OF THE INVENTION

The present invention is directed to compounds for treating memory loss and diminished cognition, particularly in the form of a dietary supplement, and methods for formulating and administering the same.

BACKGROUND OF THE INVENTION

The human brain controls all functions of the human body, including motor control; regulation of heart rate, breathing, and body temperature; emotion; executive functioning; speech and language; and the reception and processing of sensory information. As part of the nervous system, the human brain is considered the most complex living structure known in the universe, with an estimated 100 billion neurons passing signals via as many as 1,000 trillion synaptic connections. Accordingly, the brain is the most metabolically active organ in the body (by a wide margin), while representing only 2% of a human's body weight. Conversely, the brain accounts for more than 20% of the body's total energy expenditure.

The human brain is epicenter for all learning and memory and critical to healthy executive functioning and reasoning. However, its delicate nature makes the brain susceptible to many types of damage and disease. Further, as humans age, a normal amount of memory loss and diminished cognition is often realized. It would be advantageous to provide supplementation of compounds (preferably comprising one or more vitamins, herbs, and nutrients) to increase memory retention and cognition, or prevent/delay the onset of certain unresolved neurological degenerative ("neurodegenerative") diseases, such as Alzheimer's disease, Parkinson's disease multiple sclerosis and dementia, to name a few.

The growth of neurodegenerative disease is staggering. Approximately 5.5 million Americans suffer from Alzheimer's disease. Of those, approximately 5.3 million are over the age of 65 and 200,000 are under the age of 65 ("younger-onset Alzheimer's disease"). About 1 million Americans (and about 10 million people worldwide) suffer from Parkinson's disease. 400,000 people in the U.S. are diagnosed with multiple sclerosis. Other known but unresolved problems relating to brain health, include but are not limited to dementia, senile dementia, and attention deficit hyperactivity disorder.

As healthy individuals (e.g., without any of the neurodegenerative diseases listed above) age, they may still suffer memory loss, diminished cognition, decreased retention of information, mild confusion, decreased processing speed and/or decreased concentration. Historically, this has been accepted as a normal result of aging, but there is increasing evidence that indicates it may be due to health issues that are treatable. These health issues include but are not limited to medication side effects, vitamin B12 deficiency, alcoholism, tumors or infections in the brain, or some thyroid, kidney, or liver disorders. Emotional problems, such as stress, anxiety, or depression, may also cause basic memory loss. Therefore, it would be beneficial to provide a compound, such as a dietary supplement, that treats dementia, memory loss and neurodegenerative disease, and that otherwise addresses the issues identified above. It is also desirable to provide a compound comprised of certain vitamins, herbs, mushrooms, and other substances are known to assist with the production of neurons in the brain, the protection of existing neurons, and overall brain size.

The problems described above (and others) are addressed by the compositions and methods described in detail below.

SUMMARY OF THE INVENTION

The present disclosure relates to a compound, particularly in the form of a dietary supplement, which improves upon the healthy function of the brain.

In varying embodiments described herein, the present disclosure relates to a compound that is capable of treating memory loss and diminished cognition. Certain elements of the novel compounds and methods for formulating the same are described in varying levels of detail herein.

Hericium Erinaceus ("lion's mane mushroom") has been discovered to provide beneficial neuroregenerative effects as well as many other beneficial properties, particularly when administered in the manner described herein.

The applicant has also found that Bacopa Monnieri ("water hyssop") can support information retention, memory consolidation, working memory, and visual information processing (sustained attention), and is particularly well-suited for individuals suffering from the effects described in the Background of the Invention section of the application.

Additionally, Epigallocatechin-3-Gallate (EGCG) has been demonstrated to provide beneficial effects on cognition and memory, and is suitable for administration with the composition described in varying embodiments herein.

Huperzine has also been discovered to increase levels of a neurotransmitter related to memory formation, recall and many basic cognitive functions.

In addition to the problems associated with brain abnormalities described herein, certain people are also more susceptible to nutrient deficiencies. Through experimentation, it has been found that including various vitamins, such as Vitamin B12 (as Methylcobalamin) can be beneficial to people who have conditions that adversely affect their mental health. More particularly, people who are deficient in Vitamin B12 (Methylcobalamin) may have brain and neurological disorders. More than a third of psychiatric admissions have been found to be suffering deficiencies in folate or Vitamin B12. Deficiency of Vitamin B12 has been shown to cause brain fog, memory loss, depression, anxiety, confusion, disorientation, hallucinations, or schizophrenia.

Individuals deficient in Acetyl-L-Carnitine may suffer from a number of conditions, including brain fog, Fibromyalgia, ME/CFS ('myalgic encephalomyelitis' a.k.a. 'chronic fatigue syndrome'), Lyme disease, diabetes, Alzheimer's, dementia, and autism. Therefore, providing a composition that also comprises appropriate levels of Acetyl-L-Carnitine can also be beneficial.

Other nutrients and compounds can provide further benefits to the brain of the human body, and are described in greater detail herein. Methods for formulating the compound are also disclosed herein.

The unique combination of the composition is preferably administered orally in the form of a capsule. The unique combination has synergistic advantages over previously known compositions. As disclosed in more detail in the Detailed Description, the present invention provides compositions, methods for treating memory loss and diminished cognition, and methods for forming the compound.

The composition is preferably comprised of a unique and novel formulation in pre-determined amounts, and further provides benefits previously unexpected. In addition to other health benefits described herein, the composition:

supports memory, learning and intellectual performance;
provides neuroprotective effect;
improves cognitive function; and
optimizes visual information processing.

Further, this formula is provided by way of a nootropic formula, which comprises supportive nutrients for a healthy brain.

In a preferred embodiment, the composition is comprised of at least Hericium Erinaceus, Bacopa Monnieri, EGCG (Epigallocatechin-3-Gallate), Huperzine, Acetyl-L-Carnitine, Vitamin B12, and a blend of herbal components, by way of example including but not limited to Ginkgo Biloba, Phosphatidylserine, and/or Gotu Kola or combinations/subcombinations thereof. These ingredients can be included, which support memory, learning and intellectual performance.

More particularly, in one preferred embodiment of the present disclosure, the composition comprises the following, with variability in dosages listed below:

1) Hericium Erinaceus—between about 100 mg and about 1000 mg;
2) Bacopa Monnieri—between about 50 mg and about 650 mg;
3) EGCG—between about 10 mg and about 200 mg;
4) Huperzine—between about 25 mcg and about 400 mcg;
5) Acetyl-L-Carnitine—between about 100 mg and about 1000 mg; and
6) Vitamin B12—between about 50 mcg and 1000 mcg.

In certain embodiments, a blended composition may further comprise any one of the following ingredients, alone or in any combination:

7) Ginkgo Biloba—between about 10 mg and about 160 mg;
8) Phosphatidylserine—between about 10 mg and 400 mg; and
9) Gotu Kola—between about 10 mg and 500 mg.

In one embodiment, the composition is provided as a dietary supplement. In one embodiment, the composition is administered in the form of a capsule. In an alternate embodiment, the composition is administered in the form of a gummy chew, tablet, powder or liquid extract. In further embodiments, the composition comprises one or more palatability agents to favorably alter the taste of the composition for human consumption.

These and other advantages will be apparent from the disclosure of the invention(s) contained herein. The above-described embodiments, objectives, and configurations are neither complete nor exhaustive. The Summary of the Invention is neither intended nor should it be construed as being representative of the full extent and scope of the present invention.

References made herein to "the present invention" or aspects thereof should be understood to mean certain embodiments of the present invention and should not necessarily be construed as limiting all embodiments to a particular description. The present invention is set forth in various levels of detail in the Summary of the Invention and the Detailed Description, and no limitation as to the scope of the present invention is intended by either the inclusion or non-inclusion of elements in this Summary of the Invention. Additional aspects of the present invention will become more readily apparent from the Detailed Description and appended claims.

DETAILED DESCRIPTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

As used herein, the phrases "at least one", "one or more", and "and/or", as used herein, are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being modified in all instances by the term "about".

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

COMPOSITION

Hericium Erinaceus

Hericium Erinaceus, commonly known as lion's mane mushroom, is a known substance among practitioners of Chinese medicine. In a most preferred embodiment, the compound is comprised of a pre-determined amount of Hericium Erinaceus. Hericium Erinaceus is an edible and medicinal mushroom belonging to the tooth fungus group, and contains polysaccharides, including B-glucan, heteroglucans, heteroxylans, as well as several cyanthane derivative triterpenes known as hericenone and erinacine. These latter compounds are considered to be responsible for the neuroregenerative effects of this species. Nerve growth factor (NGF) has potent biological activities, such as preventing death and increasing neurite outgrowth. Scientists suspect that a deficiency of NGF is part of the pathology of Alzheimer's disease and etiology. Providing the body with NGF is not useful since they are large proteins, unable to cross the blood-brain barrier. Synthesis of NGF within the brain, however, maybe helpful. Research is being conducted to show that hericenones and erinacines may promote NGF biosenthesis and thus, neuroprotection and regeneration.

In addition to its neuroregenerative effects, it contains valuable antimicrobial, antidiabetic, antihypertensive and anti-oxidant properties. In a preferred embodiment, the composition comprises from about 100 mg to 1,000 mg of Hericium Erinaceus. In a most preferred embodiment, the composition comprises about 500 mg of Hericium Erinaceus.

Bacopa Monnieri

Bacopa Monnieri, commonly known as water hyssop, is a nootropic herb native to the wetlands of southern and Eastern India, Australia, Europe, Africa, Asia, and North and South America. Dietary supplements containing Bacopa Monnieri (also known as brahmi) can help with information retention, visual information processing (sustained attention), memory consolidation and working memory. The form of Bacopa Monnieri used in a preferred composition is referred to as brand name "Synapsa" a high-quality patented form of Bacopa Monnieri. Bacopa Monnieri works by inhibiting acetylcholinesterase, activating choline acetyltransferase, and increasing cerebral blood flow. Research and investigation suggests that Bacopa Monnieri extracts may have protective effects in animal models of neurodegeneration. In addition, experimentation has shown that supplementation with Bacopa Monnieri can increase processing and decision-making speed in a multitasking environment.

In a preferred embodiment, the composition comprises from about 50 to 650 mg of Bacopa Monnieri, preferably "Synapsa" brand. In a most preferred embodiment, the composition comprises about 320 mg of Bacopa Monnieri.

EGCG (Epigallocatechin-3-Gallate)

Epigallocatechin-3-Gallate, or EGCG, is a phytochemical found in green tea. Studies on EGCG demonstrate its beneficial effects on cognition and memory. ECGC contains powerful antioxidant effects against free radicals, unstable molecules that can damage healthy cells and MLS cause cancer as a result. Consuming green tea has also been found through experimentation to support weight loss by promoting diet-induced thermogenesis and fat oxidation. In addition, it may have preventative cardiac benefits against heart disease, hypertension and stroke.

In a preferred embodiment, the composition comprises from about 10 mg to 200 mg of EGCG. In a most preferred embodiment, the composition comprises about 50 mg of EGCG.

Huperzine

Huperzine is an alkaloid which is present naturally in some plant species, most commonly Huperzia serrata, or "Chinese toothed clubmoss." It contains the acetylcholinesterase inhibitor Huperzine A or more commonly abbreviated as "Hup A.". It works by increasing levels of acetylcholine, the neurotransmitter associated with memory formation, memory recall and many of the most basic cognitive functions. Research and experimentation shows it to be effective as an amino acid based treatment for dementia, cognition disorders and sometimes Alzheimer's disease. Huperzine A promotes neurogenesis & neuroplasticity in the brain.

In a preferred embodiment, the composition comprises from about 25 mcg to 400 mcg of Huperzine A. In a most preferred embodiment, the composition comprises about 100 mcg of Huperzine A.

Acetyl-L-Carnitine

Acetyl-L-Carnitine is an acetylated form of L-Carnitine. This form is best for supporting healthy mental and cognitive function while also promoting the generation of energy. It crosses the blood-brain barrier more readily than other forms of L-Carnitine. The fact that the acetylation of L-Carnitine is a normal event in the human brain may explain why greater activity is found in the brain when using Acetyl-L-Carnitine rather than other forms. L-Carnitine is an amino acid that is naturally produced by the body, although it can be administered as a dietary supplement. It helps the human body manufacture energy molecules, and has been shown to benefit cognitive ability, memory and mood. Acetyl-L-Carnitine is used for a variety of brain disorders including Alzheimer's disease, age-related memory loss, late-life depression, and secondary thinking problems related to alcoholism or Lyme disease. It is also used to help people with Down syndrome, poor circulation of blood flow in the brain, cataracts, diabetic neuropathy, and facial paralysis syndromes. In addition, men use Acetyl-L-Carnitine for infertility and age-related low testosterone levels. Some research suggests Acetyl-L-Carnitine might improve mood and decrease depression in elderly people.

Acetyl-L-Carnitine has potent antioxidant properties. It acts as a neuroprotectant, preventing and repairing damage caused by free radicals that damage brain cells. It helps the brain rid itself of toxins and may reduce cell death due to excitotoxicity, a pathological process triggered by the overactivation of glutamate receptors. It strengthens nerves and signal receptors and has been shown to protect the brain against the harmful effects of alcohol use. Additional investigations suggest it may be successful as a potential treatment for chronic fatigue syndrome.

In a preferred embodiment, the composition comprises from about 100 mg to 1,000 mg of Acetyl-L-Carnitine. In a most preferred embodiment, the composition comprises about 200 mg of Acetyl-L-Carnitine.

Vitamin B12 (Cobalamin)

Vitamin B12 deficiency is estimated to affect 40% of adults. Long-term B12 deficiency can lead to permanent nerve and brain damage, brain atrophy, dementia and Alzheimer's. Accumulating evidence shows that severe B12 deficiency may cause demyelination in the CNS or Central Nervous System.

The benefits of Vitamin B12 (cobalamin) are numerous. This coenzyme has a key role in the preservation of healthy nerve cells, red blood cell formation, energy, and DNA synthesis. It is involved in the metabolism of every cell of the human body. No plants, animals or fungi are capable of producing Vitamin B12. It is only produced by prokaryotes. Prokaryotes are just microscopic one-celled organism bacteria or cyanobacteriaa that have neither a distinct nucleus with a membrane nor other specialized organelles. They are simple organisms but they can produce B12, and in humans it is these very bacteria-our intestinal probiotics-that produce B12. Humans can ingest B12-rich foods in the form of clams, organ meats, and other proteins (i.e. animal meat) because they are the most bioavailable food sources of B12. Supplementation becomes important for people with compromised guts (intestinal permeability).

B12 is a chemical complex vitamin. Research and experimentation indicates that Vitamin B12 may help protect against brain volume loss (brain shrinking) especially in the elderly. It may be administered orally to slow down the process of memory loss, dementia, confusion, depression and Alzheimer's disease, or alternatively to boost concentration, mood, energy, cognitive function, and the immune system.

Some people diagnosed with these brain disorders make remarkable recoveries when their low B12 levels are addressed. Accumulating evidence indicates that seniors with dementia, depression, and mood disorders should have their B12 levels closely monitored for life.

Persons at risk for Vitamin B12 deficiencies include vegans, to a lesser extent vegetarians, persons regularly taking antacids or proton pump inhibitors, and those who have had bariatric surgery. Persons who suffer from autoimmune diseases such as adult onset diabetes, vitiligo, thyroid disease, Crohn's disease and other diseases in the rheumatic family such as lupus may also be at risk. In addition, people over age 50 are less able than younger people to absorb B12 from food, which may lead to deficiency.

In a preferred embodiment, the composition comprises from about 50 mcg to 1,000 mcg of Vitamin B12. In a most preferred embodiment, the composition comprises about 150 mcg of Vitamin B12.

Ginkgo Biloba

Ginkgo Biloba (*Salisburia adiantifolia*) is an extract derived from the leaf of the Chinese ginkgo tree, also known as the maidenhair tree. It has been used in traditional Chinese medicine since ancient times. Experimentation indicates that it improves memory in people with dementia. Some studies have shown that ginkgo helps improve memory and thinking in young and middle-aged healthy people who are healthy. It may be useful in the treatment of Attention Deficit Hyperactivity Disorder (ADHD). It is often used as a dietary supplement to boost memory and enhance mental performance.

The most important nutrients in Gingko are chromium, niacin (vitamin B3), selenium and zinc. Ginkgo leaves contain two antioxidants: flavonoids, which protect the nerves, heart muscle, blood vessels, and retina from damage; and terpenoids, which improve blood flow by dilating blood vessels and reducing the stickiness of platelets. Increasing evidence indicates use of Ginkgo Biloba for cerebral insufficiency (insufficient blood flow to the brain), dementia, cognitive performance, Alzheimer's, generalized anxiety disorder, and schizophrenia. In addition, it may help with poor circulation in the legs, glaucoma, and premenstrual syndrome.

In a preferred embodiment, the composition comprises from about 10 mg to about 160 mg of Ginkgo Biloba. In a most preferred embodiment, the composition comprises about 40 mg of Ginkgo Biloba. In alternate embodiments, one or more additional herbal extracts are included or substituted for Ginkgo Biloba such as vinpocetine.

Phosphatidylserine

Phosphatidylserine ("PS") is a phospholipid containing both amino acids and fatty acids, that is present in every cell of the human body. Phosphatidylserine is critical to the maintenance of all cellular function and there are many well-designed studies to support its value for age-related cognitive decline. Phosphatidylserine is required to create healthy nerve cell membranes and myelin. Myelin is the fatty covering around each nerve cell (neuron).

The aging brain is associated with biochemical alterations and structural deterioration that impair neurotransmission. Phosphatidylserine supplementation is efficiently absorbed by humans and will cross the blood-brain barrier. It may slow, halt, and/or reverse biochemical alterations and structural deterioration of nerve cell membranes. It supports human cognitive functions, including both short- and long-term memory, the ability to form new memories, the ability to retrieve old memories, the ability to learn and recall information, the ability to focus attention and concentrate, the ability to reason and solve problems, normal language skills, and the ability to word find and communicate. It also supports locomotor functions, especially rapid reactions and reflexes.

Accumulating evidence indicates that phosphatidylserine may be helpful for the treatment of ADHD (attention deficit hyperactivity disorder), depression, Alzheimer's disease, and Parkinson's disease.

In a preferred embodiment, the composition comprises from about 10 mg to about 400 mg of Phosphatidylserine. In a most preferred embodiment, the composition comprises about 50 mg of Phosphatidylserine.

Gotu Kola

Gotu Kola (*Centella asiatica*) is a perennial plant native to Asian wetlands. It is also commonly known as pennywort. It is used as a medicinal herb in Chinese medicine, Ayurvedic medicine, and orthodox western medicine.

Gotu Kola possesses cognitive benefits, but it is also used to treat anxiety, infections including UTI, skin wounds and burns, and rheumatism. It contains chemicals that decrease inflammation and decrease blood pressure in veins. A 2016 study published in *Evidence Based Complement Alternat Medicine determined that two compounds*: Asiatic acid and Madecassic acid were the dominant components of Gotu Kola's cognitive contributions. A further investigation on the pure combination of these two isolated compounds indicates that the combination extensively promotes nerve differentiation in test tube studies. The results of this study support these compounds (primarily found in Gotu Kola) as an effective method to intervene neurodegenerative diseases in which neurotrophin deficiency is involved. Neurotrophins (including BDNF) are a family of proteins that support the function of neurones, promote survival, and development of brain. Neurotrophins belong to a class of growth factors, secreted proteins that are capable of signaling particular cells to survive, differentiate, or grow. Gotu Kola contains compounds that support neurotrophin secretion.

Because of its neurotrophic benefits including an increase in neuronal growth, improvement in brain dysfunction, reduction in mental fatigue, and slowed memory loss, Gotu Kola is preferably included in this composition.

In a preferred embodiment, the composition comprises from about 10 mg to about 500 mg of Gotu Kola. In a most preferred embodiment, the composition comprises about 100 mg of Gotu Kola.

Absent Elements

In addition, the composition of a preferred embodiment is substantially free of the following common allergens: gluten, wheat, eggs, peanuts, tree nuts, dairy, sugar, corn, soy, yeast, fish and shellfish. The composition preferably does not contain artificial colors, flavors, or preservatives, and is free from magnesium stearate (a common lubricant used in the manufacture of pharmaceuticals and dietary supplements).

Additional Elements

In varying embodiments, the composition can further comprise variances in regards to encapsulation, or powder formulations. According to certain embodiments, the compositions described herein can further be provided with one or more palatability agents. These palatability agents serve to add flavor to the composition so that an effective dosage is easier to be ingested. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, yeast hydrolysates, and combinations thereof.

Methods

An aspect of the invention is a method to treat memory loss and diminished cognition with a composition comprising Hericium Erinaceus, Bacopa Monnieri, EGCG, Huperzine, Acetyl-L-Carnitine, Vitamin B12, Ginkgo Biloba, Phosphatidylserine, and Gotu Kola. The patient is treated by providing an effective amount of the composition. By way of example, between 1 and 3 capsules of the composition can be provided to a patient per day, in some embodiments 2 capsules per day. The capsules can be taken by the patient daily, preferably in the evening with dinner if it causes drowsiness or in the morning if it causes alertness.

An aspect of the invention is a method to prepare a compound to treat memory loss and diminished cognition. The method comprises providing proportional amounts of each material such that the resulting composition results in between about 100 mg and about 1000 mg of Hericium Erinaceus, between about 50 mg and about 650 mg of Bacopa Monnieri, between about 10 mg and about 200 mg of EGCG, between about 25 mcg and about 400 mcg of Huperzine, between about 100 mg and about 1,000 mg of Acetyl-L-Carnitine, and between about 50 mcg and 1,000 mcg of Vitamin B12. In some embodiments, the mixture can further comprise between about 10 mg and 160 mg of Ginkgo Biloba, between about 10 mg and about 400 mg of Phosphatidylserine; and between about 10 mg and 500 mg of Gotu Kola. The components are mixed, then can be provided to a delivery device (for example capsule).

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

Ranges have been discussed and used within the forgoing description. One skilled in the art would understand that any sub-range within the stated range would be suitable, as would any number within the broad range, without deviating from the invention.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

What is claimed is:

1. A composition for treating memory loss and diminished cognition, comprising:
   a) about 100 mg to about 1000 mg of Hericium erinaceus;
   b) about 50 mg to about 650 mg of Bacopa monnieri;
   c) about 10 mg to about 200 mg of epigallocatechin gallate (EGCG);
   d) about 25 mcg to about 400 mcg of Huperzine;
   e) about 100 mg to about 1,000 mg of Acetyl-L-Carnitine;
   f) about 50 mcg to about 1,000 mcg of Vitamin B12; and
   g) a blend, comprising:
      (i) about 10 mg to about 160 mg of Ginkgo biloba;
      (ii) about 10 mg to about 400 mg of Phosphatidylserine; and
      (iii) about 10 mg to about 500 mg of Gotu Kola.

2. The composition of claim 1, wherein the composition is provided as a dietary supplement.

3. The composition of claim 1, wherein the composition is administered orally in the form of a capsule.

4. The composition of claim 1, wherein the composition is administered orally in the form of a tablet.

5. The composition of claim 1, wherein the composition is substantially free of at least one of gluten, wheat, eggs, peanuts, tree nuts, dairy, sugar, corn, soy, yeast, fish and shellfish.

6. The composition of claim 1, further comprising at least one palatability agent, and wherein the palatability agent is selected from the group consisting of a plant oil, a plant hydrolysate, yeast, a yeast hydrolysate, and combinations thereof.

7. The composition of claim 1, wherein the composition comprises about 500 mg of Hericium erinaceus.

8. The composition of claim 1, wherein the Bacopa monnieri is "Synapsa", and wherein the composition comprises about 320 mg of Bacopa monnieri.

9. The composition of claim 1, wherein the composition comprises about 50 mg of epigallocatechin gallate (EGCG).

10. The composition of claim 1, wherein the composition comprises about 100 mcg of Huperzine.

11. The composition of claim 1, wherein the composition comprises about 200 mg of Acetyl-L-Carnitine.

12. The composition of claim 1, wherein the Vitamin B12 is methylcobalamin, and wherein the composition comprises about 150 mcg of Vitamin B12.

13. The composition of claim 1, wherein the composition comprises about 40 mg of Ginkgo biloba.

14. The composition of claim 1, wherein the composition comprises about 50 mg of Phosphatidylserine.

15. The composition of claim 1, wherein the composition comprises about 100 mg of Gotu Kola.

16. A composition for treating memory loss and diminished cognition, comprising:
   a) about 500 mg of Hericium erinaceus;
   b) about 320 mg of Bacopa monnieri;
   c) about 50 mg of epigallocatechin gallate (EGCG);
   d) about 100 mcg of Huperzine;
   e) about 200 mg of Acetyl-L-Carnitine;
   f) about 150 mcg of Vitamin B12;
   g) about 40 mg of Ginkgo biloba;
   h) about 50 mg of Phosphatidylserine; and
   (i) about 100 mg of Gotu Kola.

17. A method to treat memory loss and diminished cognition, providing a therapeutically effective amount of the composition of claim 1 to a patient in need thereof.

* * * * *